United States Patent [19]

Kamachi et al.

[11] 4,312,728
[45] Jan. 26, 1982

[54] METHOD FOR DETERMINING BOUNDARY POINTS ON ELECTROPHORETIC DENSITOGRAMS

[75] Inventors: Shinichi Kamachi, Hino; Toshihide Fujiwara, Fuchu, both of Japan

[73] Assignee: Olympus Optical Co., Ltd., Tokyo, Japan

[21] Appl. No.: 206,181

[22] Filed: Nov. 12, 1980

[30] Foreign Application Priority Data

Nov. 13, 1979 [JP] Japan .............................. 54-146836

[51] Int. Cl.³ ...................... G01N 27/26; G01N 33/16
[52] U.S. Cl. .......................... 204/180 S; 204/180 G; 204/299 R; 356/39; 356/402
[58] Field of Search ........... 204/180 G, 180 S, 299 R; 23/230 B; 424/12; 356/39, 402, 203, 202, 201, 72

[56] References Cited

U.S. PATENT DOCUMENTS

| | | | |
|---|---|---|---|
| 3,875,045 | 4/1975 | Bergrahm et al. | 204/299 R |
| 3,924,948 | 12/1975 | Thoden et al. | 356/203 X |
| 3,932,264 | 1/1976 | Haruki et al. | 204/299 R |
| 3,994,587 | 11/1976 | Yamamoto et al. | 356/203 X |
| 4,162,208 | 7/1979 | Aladjem et al. | 204/180 G |

Primary Examiner—Arthur C. Prescott
Attorney, Agent, or Firm—Cushman, Darby & Cushman

[57] ABSTRACT

A method for determining boundary points on electrophoretic densitograms comprising a bounding point judging step for locating boundary points on electrophoretic densitograms, a normal fraction judging step for judging whether or not the boundary points located by said boundary point judging step are normal, and a standard position computing step for determining standard positions on the basis of data having been judged as normal by said normal fraction judging step, said method being so adapted as to determine boundary points taking reference to the standard positions located by said standard position computing step by utilizing unknown samples for locating the standard positions and perform data processing without using standard samples.

7 Claims, 11 Drawing Figures

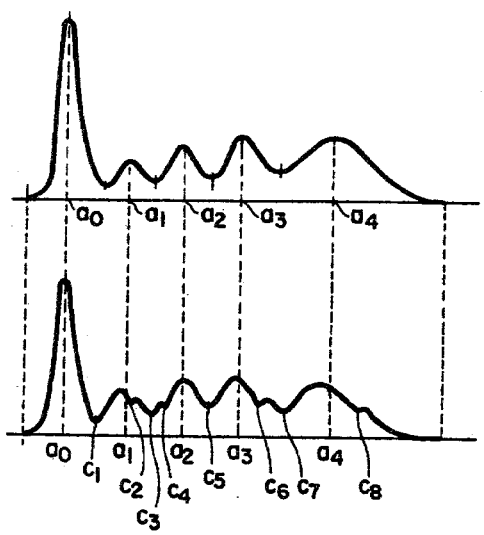
FIG. 6(A)
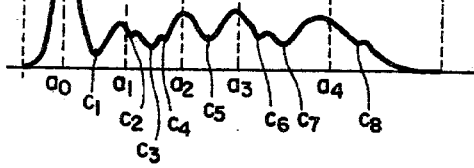
FIG. 6(B)
FIG. 7
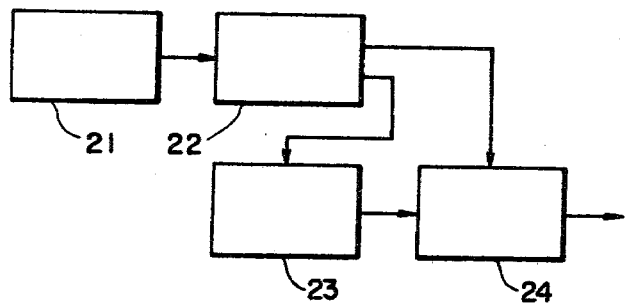
FIG. 10
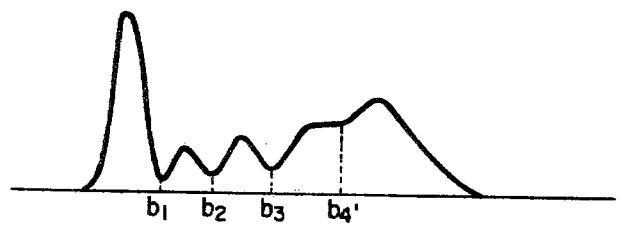

METHOD FOR DETERMINING BOUNDARY POINTS ON ELECTROPHORETIC DENSITOGRAMS

BACKGROUND OF THE INVENTION (a) Field of the Invention

The present invention relates to a method for processing fractionated patterns of serum formed by the electrophoresis.

(b) Description of the Prior Art

FIG. 1 shows basic concentration distribution (densitogram) on fractionated patterns formed by electrically energizing with an electrophretic apparatus a carrier made of cellulose acetate film onto which man's serum is applied (a healthy man's serum generally shows such patterns). Such electrophoretic patterns usually consist of five fractions of A, B, C, D and E including five peaks located at $a_0$, $a_1$, $a_2$, $a_3$ and $a_4$ corresponding to albumin, alpha 1 globulin, alpha 2 globulin, beta globulin and gamma globulin. Diagnosis or judgment whether or not the sample is normal or abnormal is done on the basis of such electrophoretic patterns and integrals or percentages of the individual fractions. However, electrophoretic densitograms actually obtained may include peaks produced by various causes in addition to the five shown in FIG. 1. The electrophoretic densitogram shown in FIG. 2, for example, has a peak located at $a_5$ in addition to the normal five peaks. This peak is produced due to turbidity in serum which allows a substance insensible of electrophoresis to remain at the position of sample application. In another example, an additional peak may be produced at a different location in addition to the five basic peaks.

When colorimetry is done on a sample which shows peaks in addition to the five basic peaks, inconvenience is caused in automatic processing with a computer of data obtained by colorimetry. FIG. 3 shows an example of configuration of a densitometer and a photometric apparatus which are currently employed. In the block diagram shown in FIG. 3, the light emitted from a light source lamps 3 is passed through a lens 4, a filter 5 and a slit 6, used for irradiating a carrier 1 and detected with a photo detector element 7. The carrier 1 has fractionated patterns 2, 2', 2'', ... of sera formed thereon as shown in FIG. 4, and is placed between the light source and the detector for photometry of the individual fractionated patterns while scanning in the direction perpendicular to the shifting direction of the carrier. That is to say, the light emitted from the light source lamp and having passed through the sample applied onto the carrier is received by the photo detector element 7, whose output corresponding to sample concentration is amplified with a preamplifier 8, converted by a logarithmic converter 9 into logarithmic value and used for preparing analog patterns as shown in FIG. 1. Successively, output from the logarithmic converter 9 is inputted into an A/D converter 10 and converted at definite time intervals into a digital signal by operating a conversion command signal generator 11 with a photometry command 11a from a computer 12. Integral or percentage of each fraction is determined on the basis of the digital data obtained at this stage.

For the operations described above, it is sufficient to determine points of local minimum values as boundary points in such a case as shown in FIG. 1 for calculating integrals or percentages of the individual fractions. In case of an electrophoretic densitogram divided into more than five fractions as illustrated in FIG. 2, however, it is impossible to determine integrals, etc. of the five fractions since five or more boundary points exist. In a case where an electrophoretic densitogram has more than five fractions, it is therefore required for the analyst to check analog patterns and fractionated patterns, and perform recalculation through processing to attribute the additional peaks to any one of the albumin fraction, alpha 1 globulin fraction, alpha 2 globulin fraction, beta globulin fraction and gamma glubulin. In case of abnormal fractions due to disease, they may be reported with no attempt made for data processing.

In view of such circumstances, there have hitherto been developed methods, for example by Japanese patent application No. 64814/79 (U.S. patent application Ser. No. 151,889), for automatic data processing to attribute additional peaks to any one of the five basic fractions even when an electrophoretic densitogram has more than five fractions. The processing disclosed by the above-mentioned Japanese patent application will be described below. In the first place, a standard serum such as a commercially available control serum is analyzed by the electrophoresis to obtain electrophoretic densitogram having five fractions. On the electrophoretic densitograms, the peak locations and boundary points remain substantially unchanged so long as type of carriers and electrophoretic conditions are kept unchanged. Therefore, unknown samples to be analyzed for clinical inspections should show densitograms having development lengths nearly the same as that of the standard serum so long as the type of the carrier and electrophoretic conditions are kept the same.

Standard lengths (distances as measured from the origin to locations of the individual peaks and the individual boundary points on the x axis) are determined as described below. A densitogram as shown in FIG. 5 is obtained by photometry of the electrophoretic patterns. Data are sampled from the densitogram at constant time intervals and subjected to A/D conversion for storing concentrations at the sampling points. The sampling points are designated consecutively as 1, 2, 3, ... n and plotted on the abscissa, and the concentrations at the sampling points are plotted along the ordinate. Based on the stored data, boundary points are to be detected. The boundary points have local minimum values on the densitogram. Let us therefore assume that an optional point on the densitogram has coordinates of $x_b$ and $y_b$. Similarly, let us assume that neighboring points on the densitogram have coordinates of $X_{b-1}$, $y_{b-1}$ and $x_{b+1}$, $y_{b+1}$ respectively. Then, a boundary point can be located as point $x_b$ which satisfies the following relation:

$$y_b < y_{b-1}, y_b < y_{b+1}$$

Let us now consider the process to locate the points $a_0$, $a_1$, $a_2$, $a_3$ and $a_4$ on the abscissa corresponding to peak tops. $a_0$ should be located between the start point $x_0$ and boundary point $b_1$, $a_1$ between the boundary points $b_1$ and $b_2$, $a_2$ between the boundary points $b_2$ and $b_3$, $a_3$ between the boundary points $b_3$ and $b_4$, and $a_2$ between the boundary point $b_4$ and end point $x_n$. In the procedures similar to those used for determining the boundary points $b_1$ through $b_4$, $a_0$ through $a_4$ can be determined as $x_a$ corresponding to points on the densitogram which have $y_a$ values satisfying the following relation:

$$y_a > y_{a-1}, y_a > y_{a+1}$$

the values of b, b, ... and a, a, ... thus determined are proportional to the lengths as measured from the start point $x_0$ to the points themselves in a relationship of 1:1. It is therefore possible to use a scale of constant time intervals in place of the lengths as measured from the start point.

The boundary points on the densitogram of the standard serum are determined as described above.

Successively, individual boundary points on a densitogram obtained on the basis of electrophoresis of an unknown sample are to be determined in the similar procedures. In case of a densitogram shown in FIG. 6 (B), for example, $c_1$, $c_2$, $c_3$ ... $c_8$ are determined as boundary points. Using the $a_0$, $a_1$, $a_2$ and $a_3$ determined on the densitogram of the standard serum shown in FIG. 6 (A) as standard points, they are located along the abscissa of the densitogram of the unknown sample as shown in FIG. 6 (B). Number of boundary points is counted in each of the sections $a_0$-$a_1$, $a_1$-$a_2$, $a_2$-$a_3$ and $a_3$-$a_4$. When the number of boundary point is counted as 1, it is adopted as a normal boundary point. When two or more boundary points are counted, the one corresponding to the lowest concentration is adopted as a normal one and the others are erased. Speaking concretely with reference to FIG. 6 (B), only one boundary point exists in the section $a_0$-$a_1$ and this is adopted as a normal boundary point. In the section $a_1$-$a_2$, three boundary points $c_2$, $c_3$ and $c_4$ exist and only $c_3$ corresponding to the lowest concentration is adopted as a normal boundary point. In the section $a_2$-$a_3$, only one boundary point $c_5$ exists and this is adopted as a normal boundary point. In the section $a_3$-$a_4$, $c_7$ is selected as a normal boundary point out of the two boundary points $c_6$ and $c_7$. In addition, all the boundary points existing in the section from $a_4$ to the end point are erased.

Boundary points produced by beta lipoprotein, beta $1_c$ protein and foreign matters at the sample application positions always correspond to concentrations higher than those corresponding to the normal boundary points. Therefore, the above-described processing method is capable of correctly determining boundary points.

FIG. 7 shows a block diagram of the above-described conventional processing method. The conventional method will be described with reference to this block diagram. In the first place, a standard serum is measured with an electrophoretic apparatus 21. The measured values obtained are fed to a boundary point judging means 22 which determines peak locations ($a_0$ through $a_4$) and boundary points ($b_1$ through $b_4$) by the above-described method. These peak locations and boundary points are transferred to a standard position storing means 23 for storing reference data. Then, an unknown sample is measured with the electrophoretic apparatus 21, and on the basis of the measured values, the boundary point judging means 22 locates the points on the abscissa corresponding to the local maximum and minimum values on the densitogram. The values thus determined are sent to a five-fraction processing means 24 which compares the data with the values of $a_0$, $a_1$, ... and $b_1$, $b_2$, ... of the standard serum stored in advance in the standard position storing means 24 for determining correct boundary points. Once the correct boundary points have been thus located, it is possible to calculate integrals or percentage of the individual fractions.

The conventional processing method described above permits locating normal boundary points even when peaks and valleys exist on densitograms in addition to the normal peaks and normal boundary points. However, this method always requires standard sera which provide normal electrophoretic densitograms without fail. Since certain standard sera commercially available cannot always provide normal electrophoretic densitograms, it is rather tedious to select proper standard sera. In addition, even when proper standard sera are selected, they may be denatured depending on conditions at the storing site or contaminated by germs, thereby incapable of being developed into the correct five fractions. Therefore, storage of standard sera pose tedious problems.

SUMMARY OF THE INVENTION

A general object of the present invention is to provide a method for processing electrophoretic data permitting locating positions of correct boundary points on densitograms without using a standard serum.

BRIEF DESCRIPTION OF THE DRAWINGS

FIGS. 6A and 6B illustrate densitograms descriptive of the conventional method for locating boundary points on electrophoretic densitograms;

FIG. 7 illustrates a block diagram descriptive of the conventional method for processing electrophoretic densitograms;

FIG. 10 illustrates an electrophoretic densitogram having a point of inflection in the vicinity of a boundary point.

DETAILED DESCRIPTION OF THE PREFERRED EMBODIMENTS

Figure 1:
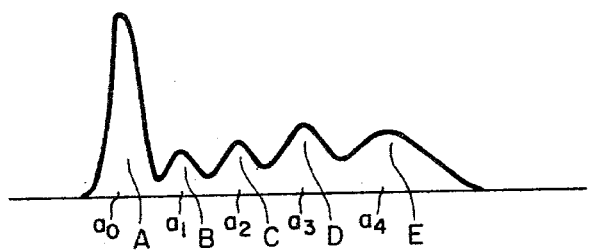
FIG. 1 shows a densitogram illustrating patterns obtained by electrophoresis of a standard sample.
Figure 2:
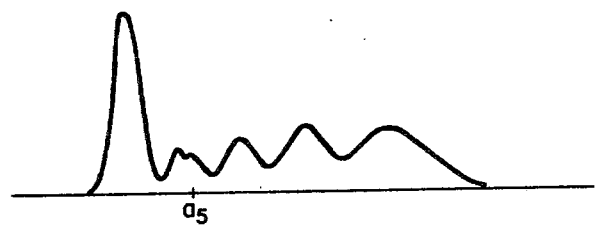
FIG. 2 shows a densitogram illustrating an example of electrophoretic patterns including fractions in addition to the standard fractions.

Now, the present invention will be described in more details with reference to the block diagram shown in FIG. 8. In this drawing, the reference numeral 23' represent a section corresponding to the standard position storing means 23 used in the conventional example and constituting the characteristic of the processing method according to the present invention. The method according to the present invention remains unchanged from the conventional method illustrated in FIG. 7 in that measured values of analyzed sample are determined by the electrophoretic apparatus 21, and that local maximum and minimum values are determined by the boundary point judging means 22. The values thus determined by the boundary point judging means are fed into a normal fraction judging means 25 arranged as a part of the standard position storing means 23' which judges whether or not the measured densitogram has normal five fractions. The judging method is as described below. In the first place, the data fed from the boundary point judging means 22 are checked to see whether or not five fractions are included. Then, integrals of concentrations of the fractions divided by the individual boundary points are calculated and the integrals are checked to see if they are within predetermined ranges. Only data that the judged as having the normal five fractions by the normal fraction judging means 25 are fed to a standard position computing means 26 which calculates reasonable standard positions on the basis of these data through statistical processing described later. The standard positions thus calculated are fed to a standard position storing means 27 arranged at the next stage for storing the data. The standard positions stored at this stage correspond to the standard positions on densitogram of standard serum stored in the standard position storing means 23 of the conventional example shown in FIG. 7.

In the next place, the data are transferred from the boundary point judging means 22 for analyzed sample to a five-fraction processing means 24 which compares the data with the standard positions stored in the standard position storing means 27 and fed through a switching means 28, and the five-fraction processing means 24 outputs data divided by correct boundary points for calculating integrals of concentrations of the individual fractions.

The method according to the present invention described above permits utilizing data obtained from normal samples among unknown samples for determining standard positions, thereby eliminating the necessity to prepare standard samples.

Figure 8:
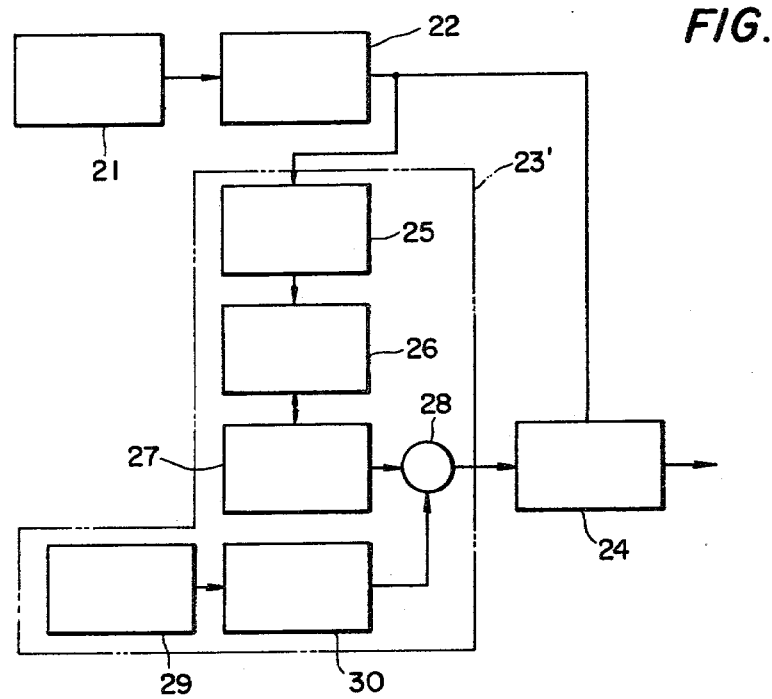
FIG. 8 illustrates a block diagram descriptive of a first embodiment of the method for processing electrophoretic densitograms according to the present invention.

In FIG. 8, the reference numeral 29 represents a manual setting means and the reference numeral 30 designates a manual setting storing means. By switching the switching means 28, the standard positions inputted into the manual setting means 29 and stored in the manual setting-storing means 30 are fed into the five-fraction processing means 24 and compared with the data supplied from the boundary point judging means 22 for outputting correct boundary points.

Out of the processes of the above-described method according to the present invention, examples of judgement whether or not fractions are normal by the normal fraction judging means 25 will be described. As is already described above, it is known that integrals of the individual fractions (actually, percentages of integral of concentrations of the individual fractions relative to integral of total concentration) of a normal man's serum are generally within certain definite ranges. Therefore, these ranges are used judging normal fractions by the normal fraction judging means 25. As another example, there is available a means to calculate ratio of integrals of concentrations of two different fractions of one and the same sample (for example, albumin fraction and alpha 1 globulin) and check to see if this ratio is within a certain definite range.

Now, calculating method in the standard position computing means 26 will be described. As an example of computing method, there is available a method to determined average values on the abscissa of local maximum and minimum values of data which have been judged as normal by the normal fraction judging means 25. As another method, it is possible to determine a median and take this value as a standard position. Even on electrophoretic densitograms of normal men'sera, local maximum and minimum values are different depending on the individual men. Therefore, positions of the local maximum and minimum points are variable rather widely even on data which have been judged as normal by the fraction judging means 25. Since it is generally possible to obtain reasonable standard values by averaging numerous data, the standard values can be made more adequate by eliminating data having values largely deviated from the standard values. Therefore, data having values largely deviated from average values may be eliminated in calculation by the standard position computing means 26 even when said data have been judged as normal by the fraction judging means 25.

Now descriptions will be made on the manual setting means. In the manual setting means 29, resonable standard positions matched with groups of unknown samples to be analyzed, types of carrier to be used, environment at the measuring site, etc. are set and the standard positions stored in the manual setting storing means are memorized. When, for example, data have not been inputted into the standard position storing means 27 and therefore a standard positions have not been stored yet, the switching means 28 is switched to the manual side, whereby the five fraction processing means 24 compares the data of the sample analyzed with the standard positions stored in the manual setting storing means 30 to prepare fraction data output. While the data of the unknown samples analyzed are being subjected to the five fraction processing by using the standard positions stored in the manual setting storing means 30 in this way, the standard positions determined based on data of samples having normal fractions are stored in the standard position storing means, whereafter the switching 28 is switched to the side of the standard position storing means 27 so as to perform processing using the standard positions stored in the standard position storing means 27. When the standard positions stored in the standard position storing means 27 are prepared on the basis of a small number of data, the standard positions are not necessarily adequate. Therefore, it is desirable to switch the switching means 28 from the side of the manual setting-storing means 30 to the side of the standard position storing means 27 after repeating processing to a certain degree by using the standard positions stored in the manual setting-storing means until the standard positions are prepared on the basis of a relatively large number of data.

Figure 9:
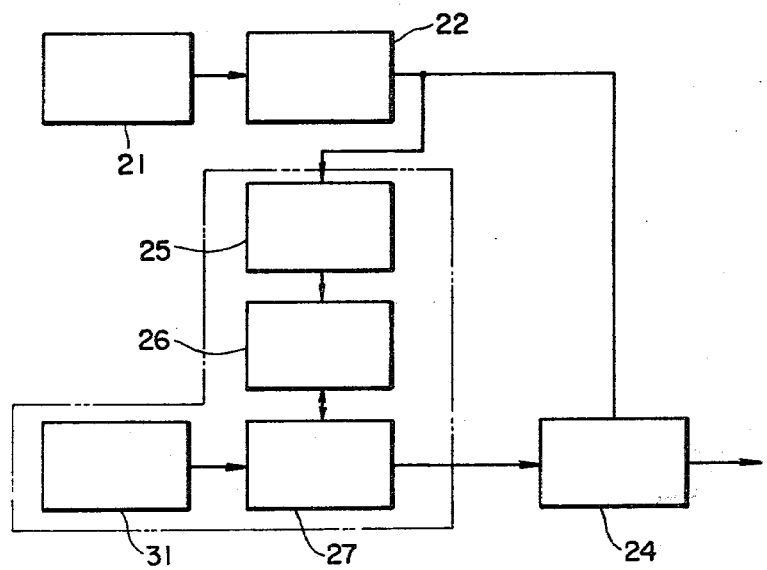
FIG. 9 illustrates a block diagram descriptive of a second embodiment of the method for processing electrophoretic densitograms according to the present invention.

FIG. 9 show a block diagram illustrating a second embodiment of the method according to the present invention. In this embodiment, an initial value setting means 31 is used in place of the manual setting means 29 and manual setting-storing means 30 adopted for the embodiment shown in FIG. 8, the other means being substantially the same as those used in the embodiment shown in FIG. 8. In this embodiment, when the data processing system is started, reasonable standard positions stored in the initial value setting means are compared with data obtained by analyzing an unknown sample to output fractioned data from the five-fraction processing means 24. This processing for a definite number of times and then the switching means 28 is switched in order to perform data processing by using the standard positions stored in the standard position storing means 27 at the subsequent stages. In addition, the initial value setting means 31 may be so designed as to be selectable as occasion demands.

For carrying out the above-described method according to the present invention, the fraction processing performed by the five-fraction processing means 24 on the basis of the stored standard positions and data obtained by analyzing unknown sample is not limited to the method described as the conventional example, but can carried out, for example, as described below:

(1) Taking a point on the abscissa corresponding to each individual peak top stored in the standard position storing means 27 as standard, to adopt a local minimum point nearest the standard point (point on the abscissa corresponding to the standard local minimum point) as the normal boundary point when two or more local minimum points exist between a pair of standard positions (corresponding to peaks).

(2) While ignoring standard positions corresponding to peak tops, to compare the standard positions corresponding to local minimum values with points on the abscissa corresponding to local minimum values on densitogram of unknown sample analyzed and adopt the points on the abscissa nearest the standard positions as normal boundary points.

(3) On electrophoretic densitograms, local minimum points may not appear at locations where they should originally exist. On the electrophoretic densitogram shown in FIG. 10, for example, an S-shaped curve appears in the vicinity of $b_4'$ at which a local minimum point should originally exist. In such a case, a point of inflection is to be located and the point on the abscissa corresponding to this point of inflection is to be adopted as a boundary point. When an electrophoretic densitogram shows three or less local minimum points, there is available a method to locate point(s) of inflection to add boundary point(s).

Figure 3:
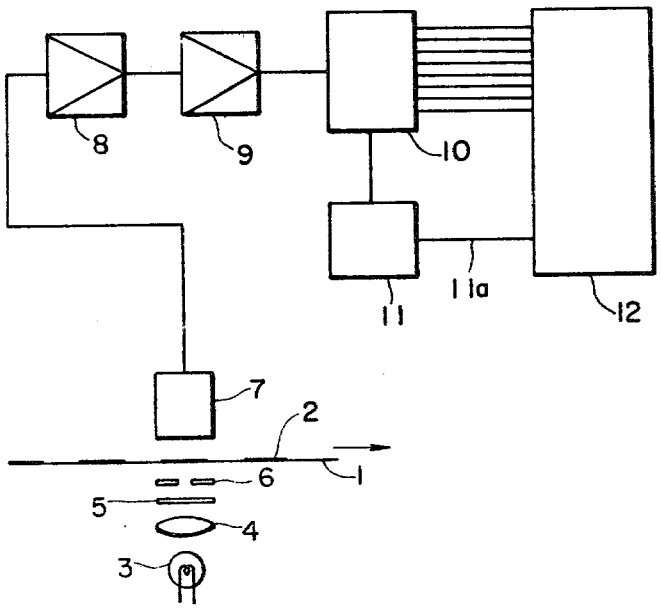
FIG. 3 shows a block diagram illustrating configuration of a system used for processing electrophoretic fractionated patterns.
Figure 4:
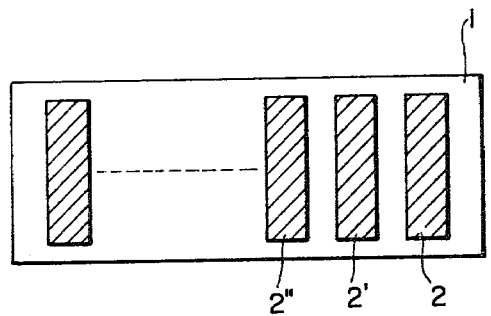
FIG. 4 shows a schematic diagram illustrating a carrier on which fractionated patterns are developed.
Figure 5:
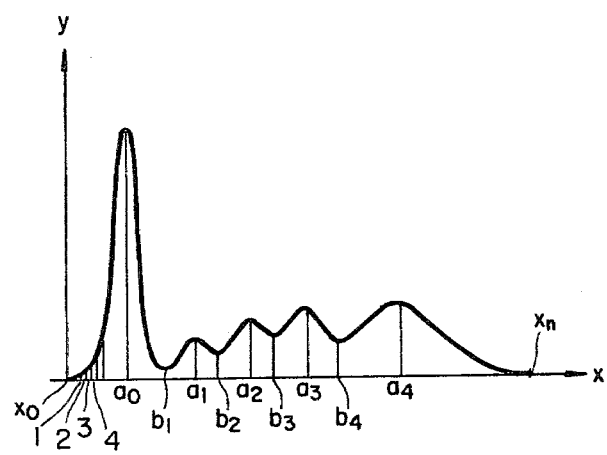
FIG. 5 shows a densitogram descriptive of a method to determine locations of peak tops and boundary points on an electrophoretic densitogram.

All the processing stages by the individual means adopted for the above-described method according to the present invention can be performed by a computer and a program prepared therefore. Speaking concretely, the electrophoretic apparatus 21 can be controlled with a computer in the manner described as the conventional example with reference to FIG. 3. Further, the data processing by the boundary point judging means 22 for locating local minimum and maximum values, etc. can be performed through differential calculations, etc. with a computer. The processing by the normal fraction judging means 25 to judge whether or not a densitogram has five normal fractions and whether concentration integrals of the individual fractions are within a predetermined ranges can be performed with a computer. The processing by the standard position calculating means 26 is to compute average values or median on the abscissa corresponding to the local maximum and minimum values of plural fractions. That is to say, the processing is performed to locate points on the abscissa corresponding to local maximum and minimum values which are most probable on densitograms through statistical computations.

Both the standard position storing means 27 and manual setting-storing means 31 use memory devices. Further, the five-fraction processing means 24 utilizing the conventional fraction processing method or the above-mentioned processes (1), (2) and (3) is a computer means for determining the five fractions. As is clear from the foregoing descriptions, all the processing stages for the method according to the present invention can be performed with a computer. The manual setting means 29 may be equipped with input devices such as manual switches, tape reader, etc. for convenience of data inputting or memory device which can store standard positions in advance.

The above-described method according to the present invention is so adapted as to use a normal fraction judging means which judges whether or not analytical data obtained by analyzing unknown samples have five normal fractions, thereby locating normal boundary points to be used as standard points through statistical processes by using analytical data judged as normal and determining boundary points on densitograms of unknown samples through comparison with the standard points. Since the standard positions are determined on the basis of data obtained from a large number of normal samples, these positions can assure high reliability. Moreover, the method according to the present invention eliminate the conventional necessity to prepare standard samples.

We claim:

1. A method for determining boundary points on electrophoretic densitograms comprising a boundary point judging step for locating boundary points on electrophoretic densitograms prepared on the basis of fractionated patterns of samples, a normal fraction judging step for judging whether or not the boundary points located by said boundary point judging step are normal boundary points, a standard position computing step for determining standard positions through statistical processing of the data having been judged as normal by said normal fraction judging step in combination with numerous data having normal fractions previously obtained, said method being so adapted as to determine boundary points on densitograms of unknown samples using said standard positions as reference.

2. A method for determining boundary points on electrophoretic densitograms according to claim 1 additionally comprising a standard position storing step for storing said standard positions.

3. A method for determining boundary points on electrophoretic densitograms according to claim 1 wherein said normal fraction judging step calculates integral of concentrations of the individual fractions and judges data having integrals within predetermined ranges only as normal.

4. A method for determining boundary points on electrophoretic densitograms according to claim 1 wherein said standard position computing step calculates average values of the boundary points on densitograms having normal fractions and adopts said values as the standard positions.

5. A method for determining boundary points on electrophoretic densitograms according to claim 1 wherein said standard position computing step determines median of the boundary points on densitograms having normal fractions and adopts said median as the standard positions.

6. A method for determining boundary points on electrophoretic densitograms according to claim 2 additionally comprising a manual setting step and a manual setting-storing step for storing the standard positions set with said manual setting step, whereby determination of boundary points taking reference to the standard positions stored in said standard position storing step is switchable to and from the determination of boundary points taking reference to the standard positions stored in said manual setting-storing step.

7. A method for determining boundary points on electrophoretic densitograms according to claim 2 comprising additionally an initial value setting step, whereby boundary points are determined taking reference to standard positions set in said initial value setting step until processing is repeated by a predetermined number of times after processing start, and then said determination mode is switched automatically to another mode in which boundary points are determined taking reference to standard positions stored in said standard position storing means.

* * * * *